United States Patent [19]

Gates

[11] Patent Number: 4,549,027
[45] Date of Patent: Oct. 22, 1985

[54] FUNGICIDAL AND PLANT GROWTH REGULANT TRIAZOLE AND IMIDAZOLE SULFIDE COMPOUNDS

[75] Inventor: Peter S. Gates, Cambridge, England

[73] Assignee: FBC Limited, England

[21] Appl. No.: 479,060

[22] Filed: Mar. 25, 1983

[30] Foreign Application Priority Data

Apr. 1, 1982 [GB] United Kingdom ............... 8209726

[51] Int. Cl.$^4$ ............ A01N 43/50; A01N 43/64; C07D 233/60; C07D 249/08

[52] U.S. Cl. .................. 548/262; 71/76; 71/92; 544/316; 546/276; 548/101; 548/336; 548/341; 568/34; 568/56

[58] Field of Search ........... 548/101, 262, 341, 336; 424/269, 245, 273 R; 71/92, 76

[56] References Cited

U.S. PATENT DOCUMENTS

| | | | |
|---|---|---|---|
| 3,812,142 | 5/1974 | Meiser et al. | 548/341 |
| 3,912,752 | 10/1975 | Meiser et al. | 548/262 |
| 4,085,209 | 4/1978 | Miller et al. | 548/341 |
| 4,259,505 | 3/1981 | Sturm et al. | 548/336 |

FOREIGN PATENT DOCUMENTS

| | | | |
|---|---|---|---|
| 2640823 | 3/1977 | Fed. Rep. of Germany | 548/262 |
| 2821829 | 11/1979 | Fed. Rep. of Germany | 71/92 |
| 2943631 | 5/1980 | Fed. Rep. of Germany | 542/262 |
| 0124769 | 9/1980 | Japan | 424/269 |
| 0150675 | 9/1982 | Japan | 548/262 |

Primary Examiner—Alton D. Rollins
Attorney, Agent, or Firm—Lawrence Rosen

[57] ABSTRACT

Compounds of formula

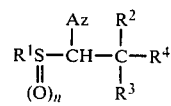

where Az is 1-imidazolyl or 1-(1,2,4-triazolyl); $R^1$ is aryl or optionally substituted alkyl; $R^2$ and $R^3$, which may be the same or different, are hydrogen or alkyl or, together with the carbon to which they are attached, form a 5 to 7 membered ring which may contain one or more oxygen atoms and which may be substituted, or when Az is 1-(1,2,4-triazolyl) can together with the carbon to which they attached form a carbonyl group; $R^4$ is aryl, substituted alkyl or aryloxy, or when $R^2$ and $R^3$ form an oxygen containing ring, can be hydrogen or unsubstituted alkyl; and n is 0, 1 or 2; together with acid addition salts, quaternary ammonium salts and complexes of these compounds with metal salts have fungicidal and plant growth regulant activity.

1 Claim, No Drawings

FUNGICIDAL AND PLANT GROWTH REGULANT TRIAZOLE AND IMIDAZOLE SULFIDE COMPOUNDS

This invention relates to compounds having use in agriculture.

There are many disclosures of compounds having fungicidal activity in which an unsubstituted triazole or imidazole group is attached to a methylene group. In very few of the disclosures, however, is a sulphur containing group attached to the same methylene group. GB Pat. No. 1419734 relates to compounds of formula

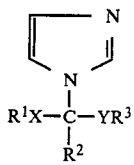

in which $R^1$ and $R^3$ can be inter alia, optionally substituted alkyl, or aryl, $R^2$ can be hydrogen, X is oxygen or sulphur and Y can be carbonyl. These compounds are said to have fungicidal activity. Of the specific compounds where X is sulphur, none is disclosed in which $R^1$ is alkyl. In Japanese Kokai No. 57/150675 compounds of formula

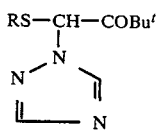

in which R is alkyl, benzyl or optionally substituted phenyl, are claimed to have fungicidal activity. In European Patent specification No 752 compounds of formula

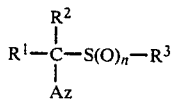

in which inter alia, $R^1$ is alkyl or aryl; $R^2$ is hydrogen; $R^3$ is alkyl, aryl or aralkyl; Az is imidazolyl or triazolyl and n is 0 to 2 are said to have fungicidal activity. It is also disclosed in European Pat. No. 5754 that these compounds have plant growth regulant activity. We have now found that a novel group of sulphur containing compounds comprising an imidazolyl or triazolyl group have both fungicidal and plant growth regulant activity.

The invention provides a compound of formula I

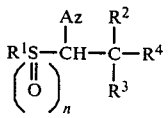

where

Az is 1-imidazolyl or 1-(1,2,4-triazolyl); $R^1$ is aryl or optionally substituted alkyl;

$R^2$ and $R^3$, which may be the same or different, are hydrogen or alkyl or, together with the carbon to which they are attached, form a 5 to 7 membered ring which may contain one or more oxygen atoms and which may be substituted, or, when Az is 1-(1,2,4-triazolyl) can together with the carbon to which they attached form a carbonyl group;

$R^4$ is aryl, substituted alkyl or aryloxy, or when $R^2$ and $R^3$ form an oxygen containing ring, can be hydrogen or unsubstituted alkyl; and n is 0, 1 or 2, together with acid addition salts, quaternary ammonium salts and complexes of these compounds with metal salts.

The complexes are usually with a salt of formula $MA_2$ in which M is a divalent metal cation, e.g. copper, calcium, cobalt, nickel or preferably manganese, and A is an anion, e.g. chloride, nitrate or a hydrocarbon sulphonate e.g. dodecylbenzenesulphonate. The molar ratio of the compound to metal salt is usually 2 or 4 to 1. Acid addition salts are usually formed with strong inorganic or organic acids e.g. hydrochloric acid or oxalic acid. Generally however the compounds are used as the free base.

Aryl groups are usually optionally substituted phenyl but may also include other aromatic groups such as naphthyl and heterocyclic aromatic groups which may be substituted, such as pyridyl, pyrimidyl, triazolyl, imidazolyl, thienyl and furanyl. When the aryl is substituted, the substituents may include halogen, hydroxy alkyl, alkoxy, cyano, nitro, aryl (alkylsulphonyloxy, alkanoxyloxy (optionally substituted, e.g. by thiocyanato) or aryloxy. Preferred substituents are halogen, especially chlorine. Any alkyl and alkoxy groups are generally of 1 to 8 carbon atoms and may be substituted e.g. by halogen, especially fluorine or chlorine, alkoxy, alkoxycarbonyl or aryl. When $R^1$ is alkyl, it is preferably tertiary alkyl, e.g. of 4 to 8 carbons, preferably t-butyl. When $R^2$ and $R^3$ form a ring this is preferably a 1,3-dioxolane ring. Substituents, when present, are usually optionally substituted alkyl or aryl.

A preferred group of compounds are those where $R^1$ is aryl or an optionally substituted tertiary alkyl group; $R^2$ and $R^3$, which may be the same or different, are hydrogen or alkyl or, together with the carbon to which they are attached, form a 5 to 7 membered ring which may contain one or more oxygen atoms and which may be substituted; $R^4$ is aryl or, when $R^2$ and $R^3$ form an oxygen containing ring, may also be optionally substituted alkyl.

A particularly preferred group of compounds are those in which n is O, $R^1$ is phenyl, optionally substituted by one or two chlorine atoms, or is tertiary butyl, $R^2$ and $R^3$ are both methyl or, together with the carbon to which they are attached, form a 1,3-dioxolane ring and $R^4$ is phenyl or 4-chlorophenyl.

The compounds of the invention have activity as fungicides, especially against fungal diseases of plants, e.g. mildews, such as powdery mildews and particularly barley powdery mildew (*Erysiphe graminis*), rice blast (*Pyricularia oryzae*), wheat brown rust (*Puccinia recondita*) and potato blight (*Phytophthora infestans*).

The invention thus also provides a method of combating fungi at a locus infested or liable to be infested therewith, which comprises applying to the locus a compound of formula I.

Some of the compounds of the invention are effective in controlling the growth of a wide variety of crops, especially to cause height reduction without any detrimental effect on the health and vigour of the plants. The invention thus also includes a method of controlling plant growth by applying to the plant a growth regulating amount of a compound of formula I. This aspect of the invention is applicable to both mono- and dicotyledonous plants, e.g. mung beans, soybeans, barley, wheat, rice, sugarbeet, cotton, sunflowers, pot plants, such as chrysanthemums, turf grass, top fruit (e.g. apples), vegetables and woody ornamentals. In some cases, the products can encourage the formation of extra shoots or tillers e.g. on cereals. Some of the compounds also have herbicidal activity.

The invention also provides an agricultural composition comprising a compound of formula I in admixture with an agronomically acceptable diluent or carrier.

The composition of the invention may of course include more than one compound of the invention.

In addition the composition can comprise one or more additional active ingredients, for example compounds known to possess plant-growth regulant, herbicidal, fungicidal, insecticidal or acaricidal properties. Alternatively the compounds of the invention can be used in sequence with the other active ingredient. Fungicides which can be used in conjunction with the compounds of the present invention include maneb, zineb, mancozeb, thiram, ditalimfos, tridemorph, fenpropimorph, imazalil, propiconazole, triadimefon, triadimenol, diclobutrazol, fluotrimazole, ethirimol, fenarimol, nuarimol, triforine, pyracarbolid, tolclofos-methyl, oxycarboxin, carbendazim, benomyl, thiophanate, thiophanate-methyl, thiabendazole, propineb, metalaxyl, dicloran, dithianon, fuberidazole, dodine, chlorothalonil, cyprofuram, dichlofluanid, sulphur, copper compounds, iprodione, ziram, nabam, prochloraz (and metal complexes of these e.g. the manganese chloride complex), zineb-ethylene thiuramsulphide adduct, captan, captafol, benodanil, mepronil, carboxin, guazatine, validamycin, vinclozolin, tricyclazole, quintozene, pyrazophos, furmecyclox, propamocarb, procymidone, kasugamycin, furalaxyl, folpet, fenfuram, ofurace, etridiazole, phosethyl aluminium and benalaxyl. Plant-growth regulants with which the products can be mixed include chlormequat, mepiquat, ethephon, paclobutrazol, dikegulac-sodium, gibberellic acid, ancymidol, maleic hydrazide, mefluidide and daminozide.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkyl-naphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of fungicidal, plant growth regulant and similar compounds, for example, a solution, a dispersion, an aqueous emulsion, a dusting powder, a seed dressing, a fumigant, a smoke, a dispersible powder, an emulsifiable concentrate or granules. Moreover it can be in a suitable form for direct application or as a concentrate or primary composition which requires dilution with a suitable quantity of water or other diluent before application.

As a dispersion, the composition comprises a compound of the invention dispersed in a liquid medium, preferably water. It is often convenient to supply the consumer with a primary composition which can be diluted with water to form a dispersion having the desired concentration. The primary composition can be provided in any one of the following forms. It can be a dispersible solution which comprises a compound of the invention dissolved in a water-miscible solvent with the addition of a dispersing agent. A further alternative comprises a compound of the invention in the form of a finely ground powder in association with a dispersing agent and intimately mixed with water to give a paste or cream which can if desired be added to an emulsion of oil in water to give a dispersion of active ingredient in an aqueous oil emulsion.

An emulsifiable concentrate comprises a compound of the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively it comprises the active ingredient adsorbed or absorbed on a pre-granular diluent, for example, Fuller's earth, attapulgite or limestone grit.

A wettable powder usually comprises the active ingredient in admixture with a suitable surfactant and an inert powder diluent such as china clay.

Another suitable concentrate is a flowable suspension cencentrate which is formed by grinding the compound with water, a wetting agent and a suspending agent. The concentration of the active ingredient in the composition of the present invention, as applied to plants is preferably within the range of 0.01 to 3.0 percent by weight, especially 0.01 to 1.0 percent by weight. In a primary composition the amount of active ingredient can vary widely and can be, for example, from 5 to 95 percent by weight of the composition.

In the method of the invention the compound is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill at the seeds. A suitable applications rate is within the range of from 0.05 to 20 kg per hectare, more preferably from 0.1 to 10 kg per hectare.

Alternatively the active compound can be applied directly to the plant by, for example, spraying or dusting either at the time when the fungus has begun to appear on the plant or before the appearance of fungus as as protective measure. In both such cases the preferred mode of application is by foliar spraying. It is generally important to obtain good control of fungi in the early stages of plant growth as this is the time when the plant can be most severely damaged. For cereal crops such as wheat, barley and oats it is often desirable to spray the plant at or before growth stage 5 although additional treatments by spraying when the plant is more mature can augment resistance to the growth or spread of fungi. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.01 to 10 kg. per hectare, preferably from 0.05 to 5 kg per hectare.

When the compounds of the invention are used as growth regulators they are usually best applied during the vegetative stages of growth at similar rates as above. In the case of crops such as legumes, cotton and sunflowers, application preferably takes place during the vegetative stage of growth or just prior to or just after the onset of flowering. In the case of cereals, pot plants and turf, earlier application, during the early vegetative stage of growth, is more appropriate.

The compounds of the invention, in which n is 0, may be prepared by reacting a compound of formula II

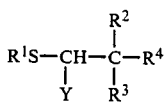

where Y is halogen, preferably chlorine, with a compound of formula AzH. This reaction is preferably carried out under basic conditions, e.g. in presence of an alkali metal carbonate, such as potassium carbonate, and optionally in the presence of an alkali metal iodide. An organic solvent is usually present, e.g. xylene or a nitrile, such as acetonitrile or a ketone, such as ethyl methyl ketone. The reaction is usually carried out at a temperature of 50° to 200° C., and generally under reflux.

Compounds in which n is 1 may be obtained by oxidising compounds of formula I in which n is 0. Compounds in which n is 2 may be obtained by oxidising compounds of formula I in which n is 0 or 1. As oxidising agent there may be used a per acid, e.g. 3-chloroperbenzoic acid. The molar amount of oxidising agent will usually determine the degree of oxidation.

The compounds of formula II may be prepared by halogenating, e.g. with N-chlorosuccinimide or sulphuryl chloride, a compound of formula III

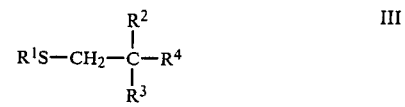

Compounds of formula III, in their turn, may be prepared by reacting a compound of formula IV

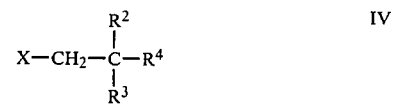

where X is halogen, preferably chlorine or bromine, with a compound, R$^1$SH, preferably under basic conditions.

Salts can be prepared by reacting the free base with a suitable acid e.g. hydrochloric acid. Complexes can be prepared by reacting the base with a suitable metal salt e.g. manganese (II) chloride.

The invention is illustrated in the following Examples. Structures of isolated novel compounds were confirmed by elemental and/or other appropriate analyses.

EXAMPLE 1

Sodium methoxide (21 g) was added portionwise to a cooled solution of 4-chlorobenzenethiol (52 g) in dimethyl formamide (180 ml), with stirring, under nitrogen. After 10 minutes, 2-methyl-2-phenylpropyl chloride (60.5 g) was added and the mixture heated slowly to reflux (130° C.). Boiling under reflux was continued for 5 hours. The mixture was then added to ice-water and the product extracted into ether. The ether solution was washed with water, aqueous sodium hydroxide and water again (twice), dried over magnesium sulphate and evaporated under reduced pressure. The residue was distilled to give 4-chlorophenyl(2-methyl-2-phenylpropyl)sulphide, b.p. 130°-155° C./0.02 mm.

N-chlorosuccinimide (43.5 g) was added portionwise with stirring to a solution of the previous product (87 g) in carbon tetrachloride (300 ml) at about 75° C. (just below reflux) with intermittent cooling. The mixture was boiled under reflux with stirring for five and a half hours, then cooled, filtered and evaporated under reduced pressure to give crude 4-chlorophenyl(1-chloro-2-methyl-2-phenylpropyl)sulphide. This product (25 g) was added to a mixture of imidazole (6.8 g), potassium carbonate (13.8 g) and potassium iodide (3 g) in acetonitrile (150 ml) and then boiled under reflux with stirring for 22 hours. The cooled solution was filtered and evaporated under reduced pressure. The residue was treated with ether and water, and the ethereal solution separated from the aqueous phase and from some insoluble oil, washed with water, dried over magnesium sulphate and evaporated under reduced pressure. The residue was purified on a silica gel column (using a 4:1 ether/petroleum ether (b.p. 60°-80° C.) mixture as the eluant) to give 1-[1-(4-chlorophenylthio)-2-methyl-2-phenylpropyl]-1H-imidazole, m.p. 77°-9° C.

EXAMPLE 2

To the product of Example 1 (4.4 g) in dichloromethane (50 ml) was added 3-chloroperbenzoic acid (2.64 g 85%) with stirring and ice-cooling. The mixture was allowed to stand overnight. After filtration, the solution was washed with sodium bicarbonate solution (twice) and water, dried over magnesium sulphate and evaporated under reduced pressure, leaving a colourless glass (3.8 g). This glass was treated with ether, the solution separated from some insoluble solid and evaporated under reduced pressure. The residue was recrystallised from a cyclohexane/toluene mixture to give 1-[1-(4-chlorophenylsulphinyl)-2-methyl-2-phenylpropyl]-1H-imidazole, m.p. 125°-7° C.

EXAMPLE 3

In a similar manner to Examples 1 or 2, using the appropriate starting materials, solvents and azole compound, the following were obtained. In most cases, intermediates were used unpurified, after their structures had been confirmed by n.m.r. Compounds where n=2 were obtained in a similar manner to compounds where n=1 but using approximately two and a half times the molar quantity of oxidising agent.

In those cases where the products were not obtained as solids, in an attempt to obtained crystalline material a salt was prepared by treatment with a suitable acid in an organic solvent. The free base was then prepared by treatment with aqueous sodium hydroxide in organic solvent and then recovery from the organic layer in conventional manner, although crystalline material was not necessarily formed. In some cases, where the resulting salt is a solid, a portion was kept for characterising and testing, in which case the melting point is given below. The salts are as follows HCl=hydrochloride, Ox=oxalate, Tol=p-toluenesulphonate and Ms=methanesulphonate. In the table in the column headed Az, I=1-imidazolyl and T=1-(1,2,4-triazolyl).

$$R^1-S(=O)_n-CH-C(R^2)(R^3)-R^4 \quad (Az)$$

| Ex No | n | Az | =CR²R³ | R¹ | R⁴ | mp(°C.) | Salt Type | Salt mp(°C.) |
|---|---|---|---|---|---|---|---|---|
| 3 | 0 | I | —CH₂— | 4Cl—Ph | Ph | oil | | |
| 4 | 0 | T | —CH₂— | Ph | 4Cl—Ph | oil | | |
| 5 | 0 | T | —CMe₂— | 4Cl—Ph | Ph | 90-2 | HCl | 172-5 |
| | | | | | | | Tol | 130-2 |
| 6 | 0 | I | —CH₂— | Ph | 2,4Cl₂—Ph | 90-2 | | |
| 7 | 0 | T | —CH₂— | Ph | 2,4Cl₂—Ph | 134-6 | | |
| 8 | 0 | I | —CMe₂— | 2,4,Cl₂—Ph | Ph | 83-4 | HCl | 202-4 |
| 9 | 0 | T | —CMe₂— | 2,4,Cl₂—Ph | Ph | oil | HCl | 176-83 |
| 10 | 0 | I | —CH₂— | Ph | 4Cl—Ph | 62-4 | | |
| 11 | 0 | I | —CH₂— | 2-pyridyl | Ph | oil | | |
| 12 | 1 | T | —CMe₂— | 4Cl—Ph | Ph | 133-5 | | |
| 13 | 2 | I | —CH₂— | Ph | 2,4Cl₂—Ph | 156-7 | | |
| 14 | 0 | I | 1,3-dioxolan-2-ylidene | Ph | 4Cl—Ph | 98-100 | HCl | 230-4 |
| 15 | 0 | T | 1,3-dioxolan-2-ylidene | Ph | 4Cl—Ph | 87-8 | | |
| 16 | 0 | I | 1,3-dioxolan-2-ylidene | 4Cl—Ph | 4Cl—Ph | glass | | |
| 17 | 0 | T | 1,3-dioxolan-2-ylidene | 4Cl—Ph | 4Cl—Ph | 99-100 | | |
| 18 | 0 | T | 1,3-dioxolan-2-ylidene | Buᵗ | 4Cl—Ph | 124-6 | | |

-continued

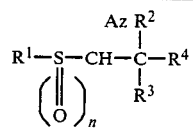

| Ex No | n | Az | =CR²R³ | R¹ | R⁴ | mp(°C.) | Salt Type | Salt mp(°C.) |
|---|---|---|---|---|---|---|---|---|
| 19 | 0 | I | (O-C-O ring) | Me | 4Cl—Ph | 106–7 | | |
| 20 | 0 | T | (O-C-O ring) | Me | 4Cl—Ph | 94–6 | | |
| 21 | 0 | I | —CMe₂— | 4Me—Ph | Ph | 82–4 | | |
| 22 | 0 | T | —CMe₂— | 4Me—Ph | Ph | oil | HCl | 182–6 |
| 23 | 0 | I | —CH₂— | 4Cl—Ph | 4Cl—Ph | 129–30 | | |
| 24 | 0 | T | —CH₂— | 4Cl—Ph | 4Cl—Ph | 66–8 | | |
| 25 | 0 | I | —CMe₂— | Ph | Ph | oil | | |
| 26 | 0 | I | —CMe₂— | 4Br—Ph | Ph | oil | | |
| 27 | 0 | T | —CMe₂— | Ph | Ph | oil | | |
| 28 | 0 | T | —CMe₂— | 4Br—Ph | Ph | 90–1 | | |
| 29 | 0 | I | (O-C(Me)-O ring) | Ph | 4Cl—Ph | oil | | |
| 30 | 0 | I | (O-C-O ring) | Ph | 4Br—Ph | 82–4 | | |
| 31 | 0 | T | —CMe₂— | 4NC—Ph | Ph | oil | HCl | 182–6 |
| 32 | 0 | T | —CMe₂— | Me | Ph | oil | | |
| 33 | 0 | I | —CMe₂— | Me | Ph | oil | | |
| 34 | 0 | I | —CMe₂— | Ph | 4Cl—Ph | oil | Ox | 198–200 |
| 35 | 0 | I | —CMe₂ | 4Cl—Ph | 4Cl—Ph | 131–3 | HCl | 207–8 |
| 36 | 0 | T | —CMe₂ | Ph | 4Cl—Ph | oil | HCl | 148–51 |
| 37 | 0 | I | (O-C-O ring) | 4Cl—Ph | Ph | 95–7 | | |
| 38 | 0 | T | —CMe₂— | 4EtOCOCHO(Me)—Ph | Ph | oil | | |
| 39 | 0 | T | —CMe₂— | 4Cl—Ph | 4Cl—Ph | oil | HCl | 170–7 |
| 40 | 0 | I | —CMe₂— | 4Buᵗ—Ph | Ph | 111–2 | | |
| 41 | 0 | T | —CMe₂— | 4Buᵗ—Ph | Ph | oil | HCl | 147–9 |
| 42 | 2 | T | (O-C-O ring) | Buᵗ | 4Cl—Ph | 176–8 | | |
| 43 | 0 | I | —CMe₂— | 2Cl—Ph | Ph | oil | | |
| 44 | 0 | T | —CMe₂— | Me | Ph | 134–6 | | |
| 45 | 0 | T | —CMe₂— | 2Cl—Ph | Ph | 89–91 | | |
| 46 | 0 | T | —CMe₂— | 2,6Cl₂—Ph | Ph | 74–5 | | |
| 47 | 0 | I | —CMe₂— | 4MeO—Ph | Ph | 84–6 | | |
| 48 | 0 | I | —CMe₂— | 2,6Cl₂—Ph | Ph | oil | | |
| 49 | 0 | T | —CMe₂— | 4 MeO—Ph | Ph | oil | | |
| 50 | 0 | I | —CMe₂— | 4Buᵗ—Ph | 4-Cl—Ph | glass | Ox | 191–3 |
| 51 | 0 | T | —CMe₂— | 4Buᵗ—Ph | 4-Cl—Ph | oil | HCl | 146–9 |
| 52 | 0 | I | —CMe₂— | 3,4Cl₂—Ph | Ph | oil | | |
| 53 | 0 | T | —CMe₂— | 3,4Cl₂—Ph | Ph | oil | | |

-continued $$R^1-S(O)_n-CH(Az)-C(R^2)(R^3)-R^4$$

| Ex No | n | Az | =CR²R³ | R¹ | R⁴ | mp(°C.) | Salt Type | Salt mp(°C.) |
|---|---|---|---|---|---|---|---|---|
| 54 | 0 | I | >C(O-)(O-) (dioxy ring) | 2,4Cl₂—Ph | Ph | oil | | |
| 55 | 0 | I | >C(O-)(O-) (dioxy ring) | Buᵗ | 4Cl—Ph | 141–2 | | |
| 56 | 0 | I | —CMe₂— | 2-pyridyl | 4Cl—Ph | glass | Ox | 173–5 |
| 57 | 0 | T | —CMe₂— | 2-pyridyl | 4Cl—Ph | glass | | |
| 58 | 0 | I | —CMe₂— | 4MeCOO—Ph | Ph | 87–9 | | |
| 59 | 0 | T | —CMe₂— | 4HO—Ph | Ph | 180–2 | | |
| 60 | 0 | I | —CMe₂— | 4HO—Ph | Ph | 166–7 | | |
| 61 | 0 | I | —CMe₂— | 4PrⁱO—Ph | Ph | 115–7 | | |
| 62 | 0 | I | >C(O-)(O-) (dioxy ring) | 4Cl—Ph | Me | oil | | |
| 63 | 0 | T | —CMe₂— | 4PrⁱO—Ph | Ph | oil | | |
| 64 | 0 | I | >C(O-)(O-)—Me (methyl dioxy ring) | Ph | 2,4Cl₂—Ph | oil | | |
| 65 | 0 | I | —CMe₂— | 4(4NO₂—Ph)—Ph | Ph | glass | | |
| 66 | 0 | T | —CMe₂— | 4(4NO₂—Ph)—Ph | Ph | glass | | |
| 67 | 0 | I | —CMe₂— | 4CF₃SO₂O—Ph | Ph | oil | | |
| 68 | 0 | T | —CMe₂ | 4CF₃SO₂O—Ph | Ph | oil | | |
| 69 | 0 | I | >C(O-)(O-) (6-mem dioxy ring) | 4Me—Ph | 4Cl—Ph | 129–31 | | |
| 70 | 0 | T | —CMe₂— | 4NCSCH₂COO—Ph | Ph | glass | | |
| 71 | 0 | I | —CMe₂— | 4MeSO₂O—Ph | Ph | 96–8 | | |
| 72 | 0 | T | >C(O-)(O-) (dioxy ring) | Ph | 4Br—Ph | 119–20 | | |
| 73 | 0 | I | >C(O-)(O-)CMe₂ (dioxy ring) | 4Cl—Ph | H | 88–9 | | |
| 74 | 0 | I | —CH₂— | 4Cl—Ph | 2,4,6Cl₃—PhO | 111–3 | | |
| 75 | 0 | T | —CMe₂ | 4MeSO₂O—Ph | Ph | 92–3 | | |
| 76 | 0 | T | —CH₂— | 4Cl—Ph | 2,4,6Cl₃—PhO | glass | | |
| 77 | 0 | T | >C(O-)(O-)CMe₂ (dioxy ring) | 4Cl—Ph | H | 113–5 | | |

-continued
$$R^1-S-CH-\underset{R^3}{\overset{Az\ R^2}{\underset{|}{C}}}-R^4$$
$$(\overset{\|}{O})_n$$
| Ex No | n | Az | =CR²R³ | R¹ | R⁴ | mp(°C.) | Salt Type | mp(°C.) |
|---|---|---|---|---|---|---|---|---|
| 78 | 0 | I | 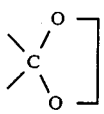 | 4Cl—Ph | Buᵗ | 81–3 | | |
| 79 | 0 | T | 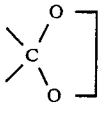 | 4Cl—Ph | Buᵗ | 98–9 | | |
| 80 | 0 | I | 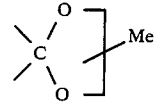 | 4Cl—Ph | 4Cl—Ph | 94–7 | | |
| 81 | 0 | I | 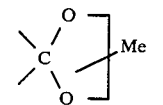 | 4Cl—Ph | 4Cl—Ph | 78–81 | | |
| | | | Isomer of Example 80 | | | | | |
| 82 | 0 | I | 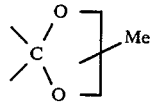 | 4Cl—Ph | Ph | oil | | |
| 83 | 0 | T | 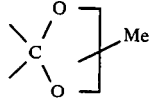 | 4Cl—Ph | Ph | oil | | |
| 84 | 0 | T | —CH₂— | Ph | 2,4,6Cl₃—PhO | 62–3 | | |
| 85 | 0 | I |  | Ph | 4Cl—Ph | 84–6 | | |
| 86 | 0 | T |  | Ph | 4Cl—Ph | oil | HCl | 152–5 |
| 87 | 0 | T | 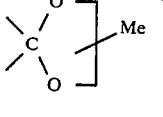 | 4Cl—Ph | 4Cl—Ph | oil | | |
| 88 | 0 | T | 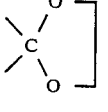 | 4Cl—Ph | Me | 85–8 | | |
| 89 | 0 | I | 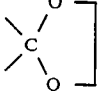 | 4Br—Ph | Me | oil | | |

-continued

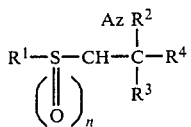

| Ex No | n | Az | =CR²R³ | R¹ | R⁴ | mp(°C.) | Salt Type | mp(°C.) |
|---|---|---|---|---|---|---|---|---|
| 90 | 0 | T | —CMe₂— | Buᵗ | Ph | oil | HCl | 135–7 |
| 91 | 0 | I | (dioxolane) | Et | 4Cl—Ph | oil | | |
| 92 | 0 | T | (dioxolane) | Et | 4Cl—Ph | oil | | |
| 93 | 0 | I | —CMe₂— | Buᵗ | Ph | oil | | |
| 94 | 0 | I | (dioxolane) | 2,4Cl₂—Ph | Buᵗ | oil | | |
| 95 | 0 | T | (dioxolane) | 2,4Cl₂—Ph | Buᵗ | oil | | |
| 96 | 0 | I | (cyclopentane) | Buᵗ | 4Cl—Ph | 113–5 | Ox | 167–9 |
| 97 | 0 | T | (cyclopentane) | Buᵗ | 4Cl—Ph | oil | HCl | 152–4 |
| 98 | 0 | I | —CMe₂— | 4 EtO—Ph | Ph | 75–6 | | |
| 99 | 0 | T | —CMe₂— | 4 EtO—Ph | Ph | oil | | |
| 100 | 0 | I | (dioxane) | 2,4 Cl₂—Ph | H | oil | | |
| 101 | 0 | T | (dioxane) | 4 Me—Ph | 4-Cl—Ph | oil | | |
| 102 | 0 | I | (dioxolane-Et) | Ph | 4Cl—Ph | oil | | |
| 103 | 0 | T | (dioxolane-Et) | Ph | 4Cl—Ph | oil | | |
| 104 | 0 | I | —CMe₂— | Ph | 2,4Cl₂—Ph | 84–7 | | |
| 105 | 0 | T | —CMe₂— | Ph | 2,4Cl₂—Ph | oil | | |

-continued

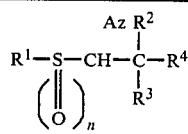

| Ex No | n | Az | =CR²R³ | R¹ | R⁴ | mp(°C.) | Salt Type | mp(°C.) |
|---|---|---|---|---|---|---|---|---|
| 106 | 0 | I | O\C(Et)/O (cyclic) | 4-Cl—Ph | Ph | 78–80 | | |
| 107 | 0 | I | O\C(Et)/O (cyclic) | 4 Me—Ph | Ph | oil | | |
| 108 | 0 | T | C=O | Buᵗ | 4Cl—Ph | 103–4 | | |
| 109 | 0 | I | —CMe₂— | N——N—Me (imidazole) | Ph | glass | | |
| 110 | 0 | I | —CMe₂— | 4-pyridyl | Ph | glass | | |
| 111 | 0 | I | —CMe₂— | Me—N——N (imidazole) | Ph | glass | | |
| 112 | 0 | I | —CMe₂— | Buᵗ | 2,4Cl₂—Ph | oil | | |
| 113 | 0 | T | —CMe₂— | Buᵗ | 2,4Cl₂—Ph | 79–80 | | |
| 114 | 0 | I | —CMe₂— | 4Cl—Ph | —CH₂OCOCH₃ | oil | | |
| 115 | 0 | T | —CMe₂— | 4Cl—Ph | —CH₂OCOCH₃ | 58–60 | | |
| 116 | 0 | I | —CMe₂— | 4Cl—Ph | —CH₂Cl | 51–3 | | |
| 117 | 0 | T | —CMe₂— | 4Cl—Ph | —CH₂Cl | oil | | |
| 118 | 0 | T | O\C/O (cyclic) | Buᵗ | Ph | 114–6 | | |
| 119 | 0 | I | —CMe₂— | 4Cl—Ph | —CH₂OH | 105–7 | | |
| 120 | 0 | T | —CMe₂— | 4Cl—Ph | —CH₂OH | 84–6 | | |
| 121 | 0 | I | —CMe₂— | pyrimidinyl | Ph | 125–7 | | |
| 122 | 0 | T | —CMe₂— | pyrimidinyl | Ph | 137–9 | | |

EXAMPLE 123

Complex No.1

A solution of cupric chloride dihydrate (1 g) in water (2 ml) was added dropwise with stirring to a solution of the product of Example 1 (6.5 g) in ethanol. The mixture was stirred overnight and the precipitate filtered off, washed with aqueous ethanol, dried and recrystallised from a dichloromethane/ether (1:1) mixture to give 1-[1-(4-chlorophenylthio)-2-methyl-2-phenylpropyl]-1-H-imidazole cupric chloride complex (4:1) m.p. 114°–8° C.

In a similar manner, complexes of the products of other examples were formed as follows.

| Complex No | Product of Example No | Metal Salt | Ratio of organic compound to metal salt | mp (°C.) |
|---|---|---|---|---|
| 2 | 22 | CuCl₂ | 4 | 162–3 |
| 3 | 34 | CuCl₂ | 4 | 115–21 |
| 4 | 35 | CuCl₂ | 4 | 97–107 |
| 5 | 36 | NiCl₂ | 4 | 183–4 |
| 6 | 33 | CoCl₂ | 2 | 177–9 |
| 7 | 18 | CuCl₂ | 2 | 98–101 |
| 8 | 50 | CuCl₂ | 4 | 112–5 |
| 9 | 18 | CoCl₂ | 4 | 186–8 |

-continued

| Complex No | Product of Example No | Metal Salt | Ratio of organic compound to metal salt | mp (°C.) |
|---|---|---|---|---|
| 10 | 18 | NiCl$_2$ | 4 | 229–31 |
| 11 | 39 | CuCl$_2$ | 4 | 123–6 |

EXAMPLE 124

The product of Example 1 also formed salts as follows

| Salt No | Type | m.p. (°C.) |
|---|---|---|
| 1 | HCl | 210–2 |
| 2 | Ox | 165–8 |
| 3 | Ms | glass |

EXAMPLE 125

This example illustrates the formation of the penultimate product (i.e. of formula II) using sulphuryl chloride.

Sulphuryl chloride (13.6 g) in carbon tetrachloride (20 ml) was added dropwise to 2,4-dichlorophenyl(2-methyl-2-phenylpropyl)sulphide (28.6 g) in carbon tetrachloride (125 ml) maintained at 23°–5° C., by cooling with water. The mixture was then stood at room temperature for two hours and evaporated under reduced pressure to give crude 2,4-dichlorophenyl(1-chloro-2-methyl-2-phenylpropyl)sulphide which was used unpurified to give the products of Example 8 and 9.

EXAMPLE 126

This example illustrates typical concentrate which can be formulated using compounds of the invention

| | % w/w |
|---|---|
| Wettable powder | |
| Product of Example 5 | 25 |
| Sodium lignosulphonate | 5 |
| Hydrous calcium silicate | 10 |
| China clay | 60 |
| Emulsifiable concentrate | |
| Product of Example 9 | 20 |
| Toximul D* | 1.5 |
| Toximul H* | 8.5 |
| Xylene to | 100 |
| Product of Example 18 | 10 |
| Calcium dodecylbenzenesulphonate | 0.27 |
| Ethoxylated castor oil | 0.73 |
| Sponto 234* | 0.9 |
| Monochlorobenzene to | 100 |

*Blends of nonionic/anionic emulsifiers.
*Blend of anionic/nonionic emulsifiers

EXAMPLE 127

Aqueous acetone suspensions of the compound under test, at various concentrations, containing 125 g per liter of polyoxyethylene sorbitan monolaurate and ethylene oxide-propylene oxide block copolymer wetting agents, were applied to the leaves (sprayed to "run-off") and to the soil surrounding the roots. (1 ml liquid/25 ml soil) of barley plants (*Hordeum vulgare*) having 2 fully expanded leaves. The treated plants together with controls, treated with aqueous solutions of wetting agent only, were inoculated 24 hours later by overhead dusting with spores of barley powdery mildew (*Erysiphe graminis*). The plants were placed in an atmosphere of 100% relative humidity for 24 hours and then transferred to a controlled environment room (18° C. and 80–90% relative humidity) for ten days after which the disease control was assessed. The final products of example 1–10, 12–41, 43, 45–58, 61–64, 66, 68, 72–87, 89, 91, 93–96 and 108; complexes 1–7 and 9–11 of Example 119; the HCl salts of Examples 1, 5, 9, 14, 31, 35, 36, 39, 51, 54 and 86; the Ox salts of Examples 1, 3, 4, 50 and 56; the Ms salt of Example 1 and the Tol salt of Example 5 gave greater than 50% control of the disease compared with the controls, at a concentration of 2000 ppm (w/v) or less.

EXAMPLE 128

In similar experiments to Example 123, products were tested for activity against (a) wheat brown rust (*Puccinia recondita*) on wheat plants (*Triticum aestivum*) having 2 fully expanded leaves—assessment being 12 days after transfer to the controlled environment room, and (b) rice blast (*Pyricularia oryzae*) on rice plants (*Oryza sativa*) having 2 fully expanded leaves—plants being placed in an atmosphere of 100% relative humidity after inoculation with aqueous spore suspension of each pathogen, and disease being assessed 7 days later. The products of the following Examples gave greater than 50% control of both disease compared with controls, at a concentration 2000 ppm(w/v) or less; Examples 8–10,12,14,15,17,23–31,34,35,38,39–41,43,45–57,61, 63,64,66,69,71,74,78,80,81,85 and 92; Complexes 1–6 8 and 11 of Example 119; the HCl salt of Examples 1, 5, 9, 14, 31, 35, 36, 39, 51, 54 and 56; the Tol salt of Example 5 and the Ms salt of Example 1. In addition activity against *Puccinia recondita* is shown by the product of Examples 1, 3–5, 6, 11, 13, 36, 37, 58 and 68; complex 10 of Example 119 and the HCl salt of Example 22; and activity against *Pyricularia oryzae* is shown by the products of Examples 38, 65, 76, 82–84, 86, 87, 89, 94 and 95. complex 7 of Example 119 and the HCl salt of Example 41 and 86.

EXAMPLE 129

Mung bean seeds were sown in pots containing coarse grade vermiculite (3–5 seeds per 6 cm pot). Five days later each pot was placed in approximately 100 ml of an aqueous dispersion of the chemical under test and shoots which had emerged were sprayed to run-off with a portion of test liquid. Ten days later the heights of the seedlings were measured and compared with control plants. Similar tests were also carried out on barley or wheat and on sunflower. The products of the following Examples gave a reduction of at least 25% in height, compared with controls, at a concentration of 100 mg/liter or less, without any adverse effects on the health and vigour of the plants.

Mung Beans

Examples 2, 3, 5, 9–11, 14–22, 25, 27,30–34, 38, 42, 44–57, 60, 62, 65, 67, 68, 72, 73, 75, 77–80, 82–84, 86–97, 99, 103 and 108; complexes 1, 2, 5–11 of Example 119; the HCl salts of Examples 1, 5, 9, 22, 31, 41, 51, 86,96 and 97; the Ox salts of Examples 34, 50 and 50; the Tol salt of Example 5 and the Ms salt of Example 1.

Barley

Examples 34, 42, 43–52, 54–62, 64–70, 72, 73, 75, 77–103 and 108; complexes 5–11 of Example 119; the HCl salts of Examples 41, 86 and 97 and the Ox salts of Examples 34, 50 and 56.

Wheat

Examples 1, 2, 5, 6, 10, 11, 14, 15, 18–21, 25, 27, 28, 30–33; complexes 1 and 2 of Example 119; the HCl salts of Examples 1, 5, 9, 14, 22 and 31; the Tol salt of Example 5 and the Ms salt of Example 1.

Sunflowers

Examples 10, 11, 18–21, 25, 30, 32, 33, 36, 37, 42, 44, 45, 47, 49, 52, 53, 55, 57–60, 62–64, 72, 73, 85, 86, 88–94 and 108; complexes 3, 5–7, 9 and 10 of Example 119; the HCl salts of Examples 1, 5 and 22; the Tol salt of Example 5 and the Ox salt of Example 34.

I claim:
1. A compound selected from
1-[1-(4-chlorophenylthio)-2-methyl-2-phenylpropyl]-1H-imidazole,
1-[1-(4-chlorophenylthio)-2-methyl-2-phenylpropyl]-1H-1,2,4-triazole,
1-[1-(2,4-dichlorophenylthio)-2-methyl-2-phenylpropyl]-1H-1,2,4-triazole, and acid addition salts or complexes thereof with a metal salt.

* * * * *